United States Patent
Shah

(10) Patent No.: US 12,133,741 B2
(45) Date of Patent: Nov. 5, 2024

(54) PREDICTING TIME TO VAGINAL DELIVERY

(71) Applicant: Birth Model, Inc., Fort Lee, NJ (US)

(72) Inventor: Anish J. Shah, Fort Lee, NJ (US)

(73) Assignee: Birth Model, Inc., Fort Lee, NJ (US)

( * ) Notice: Subject to any disclaimer, the term of this patent is extended or adjusted under 35 U.S.C. 154(b) by 0 days.

(21) Appl. No.: 18/137,099

(22) Filed: Apr. 20, 2023

(65) Prior Publication Data

US 2023/0260609 A1 Aug. 17, 2023

Related U.S. Application Data

(63) Continuation of application No. 17/887,875, filed on Aug. 15, 2022, now Pat. No. 11,664,100.

(Continued)

(51) Int. Cl.
*A61B 5/00* (2006.01)
*G06N 20/00* (2019.01)
(Continued)

(52) U.S. Cl.
CPC ........... *A61B 5/4343* (2013.01); *G06N 20/00* (2019.01); *G16H 10/60* (2018.01); *G16H 50/20* (2018.01); *G16H 50/70* (2018.01)

(58) Field of Classification Search
CPC ........ G16H 10/60; G16H 50/70; G16H 50/20; G06N 20/00; A61B 5/4343
See application file for complete search history.

(56) References Cited

U.S. PATENT DOCUMENTS 10,841,125 B2 11/2020 Cibaud et al.
10,867,245 B1 12/2020 Ghalaty et al.
(Continued)

FOREIGN PATENT DOCUMENTS

KR 101215258 1/2013
KR 20190046825 5/2019
(Continued)

OTHER PUBLICATIONS

Eggebo et al. "Sonographic Prediction of Vaginal Delivery in Prolonged Labor: A Two-Center Study," Ultrasound in Obstetrics & Gynecology, Dec. 2013, 43(2):195-201.
(Continued)

*Primary Examiner* — Jonathon A. Szumny
(74) *Attorney, Agent, or Firm* — Fish & Richardson P.C.

(57) ABSTRACT

Methods, systems, and apparatus, including computer programs encoded on a computer storage medium, for predicting the time to vaginal delivery of an infant. In one aspect, a method comprises: obtaining patient data characterizing a patient, comprising automatically querying a database storing one or more electronic medical records of the patient; generating a model input to a delivery time machine learning model based on the patient data characterizing the patient; processing the model input using the delivery time machine learning model, in accordance with values of a set of model parameters of the delivery time machine learning model, to generate a prediction for the time to vaginal delivery of the infant; and generating a notification that indicates the prediction for the time to vaginal delivery of the infant.

20 Claims, 6 Drawing Sheets

Related U.S. Application Data

(60) Provisional application No. 63/233,859, filed on Aug. 17, 2021.

(51) Int. Cl.
*G16H 10/60* (2018.01)
*G16H 50/20* (2018.01)
*G16H 50/70* (2018.01)

(56) References Cited

U.S. PATENT DOCUMENTS

| | | | |
|---|---|---|---|
| 10,943,172 B1 | 3/2021 | Tappin et al. | |
| 11,195,601 B2 | 12/2021 | Howard et al. | |
| 11,289,200 B1 | 3/2022 | Gregg et al. | |
| 11,662,351 B2* | 5/2023 | Boniface | G01N 33/689 |
| | | | 435/7.92 |
| 2002/0170565 A1 | 11/2002 | Walker et al. | |
| 2002/0193701 A1 | 12/2002 | Simpson et al. | |
| 2003/0105731 A1 | 6/2003 | Lapointe et al. | |
| 2007/0192134 A1 | 8/2007 | Littenberg et al. | |
| 2009/0012432 A1 | 1/2009 | Sharf | |
| 2010/0071696 A1* | 3/2010 | Jafari | A61B 5/087 |
| | | | 128/204.23 |
| 2010/0087719 A1 | 4/2010 | Benni et al. | |
| 2012/0041771 A1 | 2/2012 | Cosentino et al. | |
| 2012/0265549 A1 | 10/2012 | Virolainen et al. | |
| 2013/0197324 A1 | 8/2013 | Waterhouse et al. | |
| 2013/0339040 A1 | 12/2013 | Bracken et al. | |
| 2014/0279754 A1 | 9/2014 | Barsoum et al. | |
| 2015/0363569 A1 | 12/2015 | Ryan et al. | |
| 2017/0049374 A1* | 2/2017 | Eldardiry | A61B 5/165 |
| 2017/0220939 A1 | 8/2017 | Bansal et al. | |
| 2018/0063386 A1 | 3/2018 | Sharma et al. | |
| 2018/0174675 A1 | 6/2018 | Roy et al. | |
| 2018/0182474 A1 | 6/2018 | Erdmann et al. | |
| 2018/0239874 A1 | 8/2018 | Ingram et al. | |
| 2018/0333106 A1 | 11/2018 | Roberts et al. | |
| 2019/0046105 A1* | 2/2019 | Mande | G16B 25/10 |
| 2019/0133536 A1 | 5/2019 | Roberts et al. | |
| 2019/0262609 A1 | 8/2019 | Brill et al. | |
| 2020/0093988 A1 | 3/2020 | Zhong et al. | |
| 2021/0017598 A1 | 1/2021 | Jain et al. | |
| 2021/0022283 A1 | 1/2021 | Vandike et al. | |
| 2021/0106240 A1* | 4/2021 | Kerman | A61B 5/366 |
| 2021/0225052 A1 | 7/2021 | Marzorati et al. | |
| 2021/0350930 A1 | 11/2021 | Baron et al. | |
| 2022/0093229 A1 | 3/2022 | Peyman et al. | |
| 2022/0192585 A1* | 6/2022 | Bilic | A61B 5/02438 |
| 2022/0293269 A1* | 9/2022 | Pressmar | A61B 5/4343 |
| 2023/0038921 A1* | 2/2023 | Singh | G06F 18/214 |
| 2023/0140653 A1* | 5/2023 | Moufarrej | A61P 15/00 |
| | | | 435/6.11 |
| 2023/0296622 A1* | 9/2023 | Gaudilliere | G01N 33/74 |
| | | | 436/510 |

FOREIGN PATENT DOCUMENTS

| | | |
|---|---|---|
| WO | WO 2014144129 | 9/2014 |
| WO | WO 2021064858 | 4/2021 |
| WO | WO 2022036053 | 2/2022 |
| WO | WO 2022185320 | 9/2022 |

OTHER PUBLICATIONS

International Search Report and Written Opinion in International Appln. No. PCT/US2022/074952, mailed on Nov. 15, 2022, 14 pages.

Levast et al., "A Mathematical Model to Predict Mean Time to Delivery Following Cervical Ripening with Dinoprostone Vaginal Insert," Scientific Reports I, Jul. 9, 2019, 43(2) 195-201.

Liang et al., "Metabolic Dynamics and Prediction of Gestational Age and Time to Delivery in Pregnant Women," Cell 181, Jun. 25, 2020, 1680-1692.

Whattoexpect.com [online], "Is Baby Overdue? Here's What You Need to Know," May 10, 2021, retrieved from URL <https://www.whattoexpect.com/pregnancy/labor-and-delivery/what-to-do-past-your-due-date/>, 10 pages.

* cited by examiner

| Factor | Coefficients | Standard Error | t value | P-value |
|---|---|---|---|---|
| Dilation | | | | |
| Effacement | | | | |
| Fetal Station | | | | |
| Position | | | | |
| Consistency of Cervix | | | | |
| Prior Deliveries | | | | |
| Cervical Ripening | | | | |
| Augmentation of labor | | | | |
| BMI | | | | |
| Maternal Age | | | | |
| Epidural Analgesia | | | | |
| Race | | | | |
| Existence of Preeclampsia | | | | |
| Gestational Age | | | | |
| Chorioamnitisis | | | | |
| Fetal Weight | | | | |

FIG. 3

PREDICTING TIME TO VAGINAL DELIVERY

CROSS-REFERENCE TO RELATED APPLICATION

This application is a continuation to U.S. application Ser. No. 17/887,875, filed on Aug. 15, 2022, which claims priority to U.S. Provisional Application No. 63/233,859, filed on Aug. 17, 2021. The disclosure of the prior applications are considered part of and are incorporated by reference in the disclosure of this application.

TECHNICAL FIELD

This application relates predicting the time from admission to vaginal delivery of an infant using machine learning.

BACKGROUND

The overall course of induction of labor and natural labor is multifactorial. A patient's initial cervical examination, gestational age, presence of rupture of membranes, preeclampsia, chorioamnionitis and demographics may all affect the timing and success of a vaginal delivery. Due to the variables involved in labor, it is important to set expectations for the course and timing of delivery when counseling patients in the office and at the time of admission to the hospital. Unfortunately, there are few tools available that may predict the expected course of labor.

SUMMARY

This specification describes a delivery time prediction system implemented as computer programs on one or more computers in one or more locations that can generate a prediction characterizing an amount of time until a patient gives birth, e.g., through vaginal delivery.

According to a first aspect, there is provided a method performed by one or more computers, the method comprising: receiving a request to predict a time to vaginal delivery of an infant by a patient; and in response to receiving the request: obtaining patient data characterizing the patient, comprising automatically querying a database storing one or more electronic medical records of the patient; generating a model input to a delivery time machine learning model based on the patient data characterizing the patient; processing the model input using the delivery time machine learning model, in accordance with values of a set of model parameters of the delivery time machine learning model, to generate a prediction for the time to vaginal delivery of the infant; and generating a notification that indicates the prediction for the time to vaginal delivery of the infant.

In some implementations, the method further comprises, prior to receiving the request: training the delivery time machine learning model by a machine learning training technique.

In some implementations, training the delivery time machine learning model by the machine learning training technique comprises: obtaining a set of training examples, wherein each training example comprises: (i) a training model input to the delivery time machine learning model, and (ii) a target delivery time; and training the delivery time machine learning model on the set of training examples, comprising, for each training example, training the delivery time machine learning model to process the training model input of the training example to generate a predicted delivery time that matches the target delivery time for the training example.

In some implementations, the patient data characterizing the patient comprises a plurality of patient features that characterize one or more of: demographic features of the patient, features of a medical history of the patient, features characterizing a fetus of the patient, features characterizing physical characteristics of the patient, or features characterizing medical interventions applied to the patient.

In some implementations, the method further comprises: determining that an update criterion has been satisfied; and in response to determining that the update criterion has been satisfied: obtaining updated patient data characterizing the patient; and processing the updated patient data using the delivery time machine learning model to generate an updated prediction for the time to vaginal delivery of the infant.

In some implementations, determining that an update criterion has been satisfied comprises: determining that a threshold duration of time has elapsed since the time to vaginal delivery of the infant was previously predicted using the delivery time machine learning model.

In some implementations, determining that an update criterion has been satisfied comprises: determining that a value of a feature characterizing the patient has changed by at least a threshold amount since the time to vaginal delivery of the infant was previously predicted using the delivery time machine learning model.

In some implementations, the method further comprises, prior to processing the model input using the delivery time machine learning model: determining a patient category of the patient based on the patient data characterizing the patient, wherein each patient category is associated with a respective delivery time machine learning model that is specialized for predicting delivery times for patients included in the patient category; and selecting the delivery time machine learning model to be used for processing the patient data as the delivery time machine learning model associated with the patient category of the patient.

In some implementations, determining the patient category of the patient based on the patient data characterizing the patient comprises: determining the patient category of the patient based at least in part on any medical interventions applied to the patient.

In some implementations, the delivery time machine learning model includes one or more of: a neural network model, a random forest model, a support vector machine model, or a linear regression model.

In some implementations, generating the notification that indicates the prediction for the time to vaginal delivery of the infant comprises: transmitting the notification over a data communications network.

In some implementations, the method further comprises, after generating the prediction for the time to vaginal delivery of the infant: automatically interfacing with a resource reservation system to reserve one or more resources related to delivery of the infant in a time window based on the predicted time to vaginal delivery of the infant.

In some implementations, automatically interfacing with the resource reservation system to reserve one or more resources related to delivery of the infant in the time window based on the predicted time to vaginal delivery of the infant comprises: automatically reserving a delivery room in the time window based on the predicted time to vaginal delivery of the infant.

In some implementations, the method further comprises, after generating the prediction for the time to vaginal delivery of the infant: determining that vaginal delivery of the infant has not occurred within a threshold duration of time following the predicted time to vaginal delivery of the infant; and automatically generating a notification indicating that vaginal delivery of the infant has not occurred within the threshold duration of time following the predicted time to vaginal delivery of the infant.

In some implementations, obtaining patient data characterizing the patient comprises: obtaining patient data generated by one or more of: a sensor mounted on the patient, a wearable device worn by the patient, or a sensor mounted on a machine in proximity to the patient.

In some implementations, the method further comprises: generating a confidence estimate that measures a confidence of the delivery time machine learning model in the prediction for the time to vaginal delivery of the infant.

In some implementations, the method further comprises: generating a respective importance score for each of a plurality of features included in the patient data characterizing the patient, wherein the importance score for a feature measures an impact of the feature on the predicted time to vaginal delivery of the infant generated by the delivery time machine learning model.

In some implementations, the method further comprises: automatically storing the prediction for the time to vaginal delivery of the infant in an electronic medical record of the patient.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the methods described herein.

According to another aspect, there is provided a method of modeling the time to vaginal delivery of an infant to form a delivery time algorithm comprising the steps of: collecting historical patient data pertaining to vaginal delivery of an infant; determining factors of a plurality of factors that are statistically significant with respect to time to vaginal delivery of the infant; determining relationships between the factors that are statistically significant; estimating how the time to vaginal delivery of the infant changes as each of the statistically significant factors change; and deriving a delivery time algorithm (DTA) to predict an expected time to vaginal delivery of the infant using the statistically significant factors.

According to another implementation, there is provided a method of predicting the time to vaginal delivery of an infant comprising the steps of: inputting patient data for a pregnant patient into a DTA; and predicting the time to vaginal delivery of the infant using the DTA and the patient data inputted into the DTA.

In some implementations, the method further comprises interfacing with the patient's electronic medical record to retrieve the patient data prior to inputting the patient data into the DTA.

In some implementations, the method further comprises interfacing with the patient's electronic medical record to provide the predicted time to vaginal delivery to the patient's electronic medical record.

Particular embodiments of the subject matter described in this specification can be implemented so as to realize one or more of the following advantages.

The delivery time prediction system described in this specification can enable accurate estimation of an amount of time until a pregnant patient gives birth, e.g., through vaginal delivery. The delivery time prediction system can generate predicted delivery times using a machine learning model that has been trained on historical medical record data. The machine learning model implements a data-driven approach for predicting delivery times based on complex patterns and correlations in patient data well beyond what could be analyzed by a human or solely in the human mind.

The delivery time prediction system enables more efficient use of resources in a variety of ways. For instance, the delivery time prediction system can automatically reserve resources (e.g., delivery rooms) based on the predicted delivery times of patients, thus reducing overcrowding in healthcare facilities. As another example, the delivery time prediction system can automatically extract patient features from an array of electronic medical record databases to aggregate a set of patient features to be input into the machine learning model, in particular, without requiring manual intervention.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 3 is a sample table for results from a multiple linear regression of historical patient data.

Like reference numbers and designations in the various drawings indicate like elements

DETAILED DESCRIPTION

Figure 1:
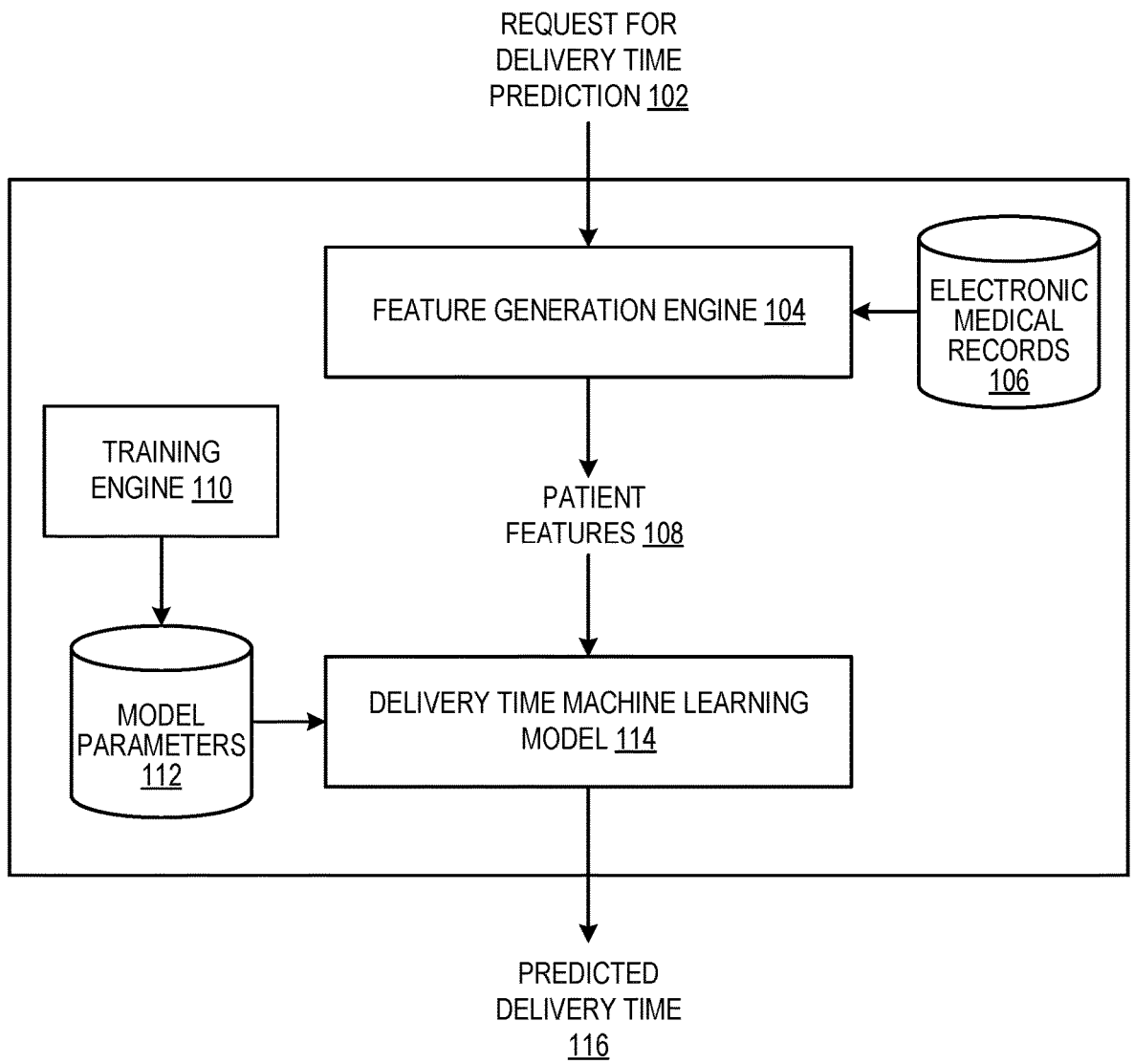
FIG. 1 is a block diagram of an example delivery time prediction system.

FIG. 1 shows an example delivery time prediction system 100. The delivery time prediction system 100 is an example of a system implemented as computer programs on one or more computers in one or more locations in which the systems, components, and techniques described below are implemented.

The system 100 is configured to receive a request 102 to generate a prediction characterizing an amount of time until a pregnant patient gives birth, e.g., through vaginal delivery (by giving birth through their vagina).

In response to receiving the request 102, the system 100 generates a predicted delivery time 116 that characterizes the amount of time until the patient gives birth.

The predicted delivery time 116 can characterize the amount of time until the patient gives birth in a variety of possible ways. For instance, the predicted delivery time 116 can predict an amount of time until the patient gives birth after the patient is admitted to the hospital. As another example, the predicted delivery time 116 can predict an amount of time until the patient gives birth after the patient enters into labor. As another example, the predicted delivery time 116 can predict an amount of time until the patient gives birth after the cervix of the patient dilates by a predefined amount, e.g., 1 cm, 2 cm, 5 cm, or any other appropriate amount. As another example, the predicted delivery time 116 can predict an amount of time until the patient gives birth measured from the current time, e.g., the time that the system 100 receives the request 102 to generate the prediction 116. More generally, the predicted delivery time 116 can characterize a predicted amount of time between: (i) a designated event prior to the patient giving birth, and (ii) the patient giving birth. In some cases, rather than specifying a particular time, the predicted delivery time 116 can specify a range of possible times, e.g., 60 minutes-90 minutes, or 8 hours-9 hours, until the patient gives birth.

The predicted delivery time 116 can be represented in any of a variety of appropriate formats. For instance, the predicted delivery time 116 can be represented as an absolute time, e.g., "10:13 PM today", or as a relative time, e.g., "5 hours and 7 minutes from the present time".

The system 100 generates the predicted delivery time 116 using a feature generation engine 104 and a delivery time machine learning model 114, which are each described next.

The feature generation engine 104 is configured generate a set of patient features 108 characterizing the patient, e.g., in response to the system 100 receiving a request 102 to generate a predicted delivery time. (Patient features can also be referred to as patient properties or patient characteristics). The patient features 108 can characterize any appropriate aspect of the patient. The patient features 108 can include, e.g., demographic features (e.g., characterizing the age, gender, race, etc., of the patient), features of the medical history of the patient (e.g., the number of times the patient has given birth previously), features characterizing the fetus (e.g., the weight of the fetus, the position of the fetus, any deformities of the fetus, the age of the fetus, etc.), features characterizing physical characteristics of the patient (e.g., the weight of the patient, the body mass index (BMI) of the patient, the level of effacement of the patient, the dilation of the patient, the level of consistency of the cervix of patient, etc.), or interventions performed on the patient during pregnancy (e.g., drugs administered to the patient, e.g., misoprostol, prostaglandin, etc.). Additional examples of patient features 108 will be described throughout this specification.

The feature generation engine 104 can generate the patient features 108, e.g., by obtaining data defining the patient features from one or more databases of electronic medical records 106. In particular, the request 102 can include data specifying the identity of the patient, and the feature generation engine 104 can query the electronic medical record databases 106 to obtain features relevant to the patient. The data specifying the identity of the patient can include, e.g., the name of the patient, the birthdate of the patient, the social security number of the patient, a medical record number of the patient, etc.

The feature generation engine 104 can be remotely located from the electronic medical record databases 106, and can transmit data to and receive data from the electronic medical record databases 106 by way of a data communications network, e.g., a local area network (LAN), a wide area network (WAN), or the internet. In particular, the feature generation engine 104 can query the electronic medical record databases 106 for data relevant to a patient, e.g., by way of an application programming interface (API) made available by the electronic medical record databases 106.

The feature generation engine 104 can query the electronic medical record databases 106 for data relevant to generating a set of patient features 108 for the patient. In some cases, the data received from the electronic medical record databases 106 can be directly included in the set of patient features. In some cases, the feature generation engine 104 may preprocess certain data received from the electronic medical record databases 106 prior to including the data in the set of patient features 108.

A few examples of techniques by which the feature generation engine 104 can preprocess data received from the electronic medical record databases 106 are described next.

For instance, the feature generation engine 104 can normalize and standardize the data, e.g., by converting parts of the data to a consistent scale, e.g., a data value representing "dilation" can be converted to a consistent scale of measurement in centimeters.

As another example, the feature generation engine 104 can obtain a collection of multiple values of a feature from the electronic medical record databases 106, determine a measure of central tendency of the feature values, and include the measure of central tendency of the feature values in the set of patient features 108. The collection of multiple feature values can be, e.g., heart rate values of the patient measured at 30 second intervals over a time window of 15 minutes.

The set of patient features can include any appropriate number of features, e.g., 10 features, 100 features, or 1000 features. The set of patient features 108 can be represented, e.g., as a vector, matrix, or other tensor of numerical values.

The delivery time machine learning model 114 is configured to process the set of patient features 108, in accordance with values of a set of model parameters 112, to generate the predicted delivery time 116 for the patient.

The machine learning model 114 can be any appropriate model, having a set of learnable model parameters, that can be configured to process a set of patient features 108 to generate a predicted delivery time 116. For instance, the delivery time machine learning model 114 can include a (multi-)linear regression model (as will be described in more detail below), a random forest model, a support vector machine (SVM) model, a neural network model, or a combination thereof.

The delivery time machine learning model 114 can be associated with a set of hyper-parameters, e.g., that define aspects of the architecture or structure of the delivery time machine learning model 114.

For instance, if the delivery time machine learning model 114 is implemented as a neural network, then the delivery time machine learning model 114 can be associated with hyper-parameters that define the types of neural network layers included in the neural network (e.g., fully connected layers, convolutional layers, attention layers, etc.), the number of neural network layers included in the neural network (e.g., 5 layers, 10 layers, or 50 layers), and the connectivity of the neural network layers included in the neural network.

As another example, if the delivery time machine learning model 114 is implemented as a random forest, then the delivery time machine learning model 114 can be associated with hyper-parameters that define the number of decision trees in the random forest, the depth of each decision tree, etc.

Generally, the hyper-parameters associated with the delivery time machine learning model 114 can have any appropriate values, e.g., such that the delivery time machine learning model 114 can have any appropriate architecture and structure.

The delivery time machine learning model 114 can generate machine learning model outputs having a variety of possible formats. For instance, the delivery time machine learning model 114 can be configured to perform regression, in particular, by directly outputting a predicted delivery time selected from a continuous range of possible delivery times, e.g., the continuous range of 0 hours to 100 hours. As another example, the delivery time machine learning model 114 can be configured to generate a score distribution over a set of possible time ranges, in particular, by generating a respective score for each time range in the set of possible time ranges. The set of possible time ranges can be, e.g., 1 minute-30 minutes, 31 minutes-60 minutes, 61 minutes to 90 minutes, etc. In this example, the delivery time machine learning model 114 can select a particular time range, e.g., that is associated with the highest score from among the set of possible time ranges, and output the selected time range as the predicted delivery time 116.

Optionally, in addition to generating the predicted delivery time 116, the system 100 can further generate a confidence estimate that characterizes a confidence of the delivery time machine learning model 114 in the predicted delivery time 116. The confidence estimate can be represented, e.g., as a numerical value in the range [0,1], where higher values can represent a higher confidence in the prediction for the delivery time. The system 100 can generate a confidence estimate in any appropriate manner. For instance, if the delivery time machine learning model 114 generates a score distribution over a set of possible time ranges (as described above), then the system 100 can generate the confidence estimate as the score assigned to the selected time range, or as the entropy of the score distribution. A confidence estimate can enable a user of the system 100 to judge the reliability of the predicted delivery time 116, and to incorporate the reliability of the predicted delivery time 116 into clinical decision making.

Optionally, in addition to generating the predicted delivery time 116, the system 100 can further generate a respective importance score for each feature in the set of patient features 108. An importance score for a feature can measure the impact of the feature on the predicted delivery time 116 generated by the delivery time machine learning model 114 for a patient. The system 100 can generate the importance scores using any appropriate technique. For instance, the importance scores can be, e.g., "SNAP" values ("Shapley additive explanations"), or "LIME" values ("local interpretable model-agnostic explanations"). The system 100 can make the importance scores (or data derived from the importance scores) available to the user, e.g., to enable the user to interpret which patient features had the greatest impact on the delivery time prediction 116.

In some implementations, the feature generation engine 104 can repeatedly update the set of patient features 108 characterizing the patient, e.g., to update the values of dynamic patient features that change over time. Each time the feature generation engine 104 generates an updated set of patient features 108, the delivery time machine learning model 114 can process the updated set of patient features 108 to generate an updated predicted delivery time 116. The delivery time machine learning model 114 may generate predicted delivery times 116 with higher accuracy as the set of patient features is updated to include more recent patient features.

The feature generation engine 104 can update the set of patient features 108 by re-querying the electronic medical record databases 106 to obtain updated values of the features included in the set of features. The feature generation engine 104 can update the set of patient features 108 (and provide the updated set of patient features 108 to the machine learning model 114 for use in generating an updated predicted delivery time 116) in response to determining that one or more update criteria are satisfied.

The feature generation engine 104 can be configured to update the set of patient features 108 in response to determining that any appropriate update criteria are satisfied. For instance, the feature generation engine 104 can update the set of patient features at fixed intervals of time, e.g., every 10 minutes. As another example, the feature generation engine 104 can scan the electronic medical record databases 106 at fixed intervals of time to determine whether the values of any of the patient features 108 have changed (e.g., by at least a threshold amount). In response to determining that the values of one or more patient features 108 have changed (e.g., by at least a threshold amount), the feature generation engine 104 can generate an updated set of patient features 108, and provide the updated set of patient features 108 to the delivery time machine learning model 114.

Patient data stored in the electronic medical record databases 106 can change over time, e.g., as the physical state of the patient changes over time. For instance, the dilation rate of the patient, the position of the fetus, consistency of the cervix and the like can over time as the delivery time draws closer.

The patient data stored in the electronic medical record databases 106 (i.e., which the feature generation engine 104 accesses to the generate the set of patient features 108) can be modified manually or automatically over time.

For instance, the patient data stored in the electronic medical record databases 106 can be manually updated by healthcare providers, e.g., based on physical examination of the patient. Healthcare providers can manually update the patient data stored in the electronic medical record databases 106, e.g., through one or more portals made available by the electronic medical record databases 106.

As another example, the patient data stored in the electronic medical record databases 106 can be automatically updated over time. In particular, one or more devices or sensors can automatically generate features characterizing physiological parameters of the patient and store the generated features in the electronic medical record databases 106. In one example, a wearable device, e.g., a smartwatch or smart wristband, can measure physiological parameters such as heart rate, systolic blood pressure, diastolic blood pressure, and store the measured physiological parameters as feature values in the electronic medical record databases 106. As another example, a body-mounted sensor can measure physiological parameters such as glucose levels or hormone levels in the blood of the patient, or fetal heart rate, or pressure of contractions, and store the measured physiological parameters as feature values in the electronic medical record databases 106. As another example, a sensor (e.g., mounted on a machine in proximity to the patient) can be measure features such as a rate at which medication is being administered to the patient (e.g., intravenously, using a titration pump). The devices or sensors can transmit the feature values for storage in the electronic medical records databases 106 by way of a data communications network, e.g., a local area network (LAN), a wide area network (WAN), or the internet. (The system 100 can thus process data generated by one or more sensors to generate a medical diagnosis, in particular, a medical diagnosis defining a predicted time to vaginal delivery of an infant).

The system 100 can use the predicted delivery times 116 generated by the delivery time machine learning model 114 in any of a variety of possible ways. A few examples applications of the predicted delivery times 116 are described next.

In some implementations, the system 100 can provide the predicted delivery times 116 to a healthcare provider, e.g., a physician, for use in planning clinical care for the patient. The system 100 can provide the predicted delivery times 116 to the healthcare provider, e.g., by way of a text message, a notification through an application, or in any other appropriate manner.

In some implementations, the system 100 can provide the predicted delivery times 116 to the patient, e.g., to allow the patient to plan on arriving at a healthcare facility at an appropriate time prior to giving birth. The system 100 can provide the predicted delivery times 116 to the patient, e.g., by way of a text message, a notification through an application, or in any other appropriate manner.

In some implementations, the system 100 can use the predicted delivery time 116 to automatically reserve resources in a healthcare facility. In particular, the system 100 can automatically reserve resources in the healthcare facility to ensure the resources are available when the patient is predicted to give birth, i.e., according to the predicted delivery time. For instance, the system 100 can automatically reserve one or more delivery rooms at a healthcare facility in a window of time based on the predicted delivery time 116. As another example, the system 100 can automatically schedule one or more healthcare providers (e.g., nurses or physicians) to be available in a window of time based on the predicted delivery time 116. The system 100 can reserve resources by interfacing with an appropriate resource reservation system, e.g., a delivery room reservation system, a staff scheduling system, or like.

In some implementations, after generating a predicted delivery time 116, the system 100 can monitor the electronic medical record databases 106 to determine if the patient gives birth within a threshold amount of time after the predicted delivery time 116. In response to determining that the patient has not given birth within the threshold amount of time after the predicted delivery time 116, the system 100 can automatically generate a notification. The system 100 can provide the notification, e.g., to a healthcare provider, e.g., by way of a text message, or through a notification in an application, or in any other appropriate manner.

The system 100 includes a training engine 110 that trains the model parameters 112 of the delivery time machine learning model 114 on a set of training examples. Each training example can include: (i) a training input to the delivery time machine learning model 114, including a set of patient features, and (ii) a target delivery time that should be generated by the delivery time machine learning model 114 by processing the training input. Each training example can be generated, e.g., based on electronic medical records for a patients that previously delivered infants.

The training engine 110 trains the delivery time machine learning model on the set of training examples using an appropriate machine learning training technique. In particular, for each training example, the training engine 110 modifies the values of the model parameters 112 of the delivery time machine learning model 114 to encourage the machine learning model to generate the target delivery time of the training example in response to processing the training input of the training example. More specifically, the training engine 110 modifies the values of the model parameters 112 of the delivery time machine learning model 114 to (approximately) minimize an error between: (i) the predicted delivery times 116 generated by the delivery time machine learning model 114, and (ii) the corresponding target delivery times specified by the training examples. The training engine 110 can measure the error between predicted delivery times and target delivery times using any appropriate error measure, e.g., a squared-error measure, or a cross-entropy error measure.

The training engine 110 can implement any machine learning training technique appropriate for training the delivery time machine learning model 114. For instance, for a delivery time machine learning model 114 implemented as a neural network, the training engine 110 can implement a stochastic gradient descent training technique. As another example, for a delivery time machine learning model 114 implemented as a linear regression model, the training engine 110 can implement a least-squares minimization training technique.

The training engine 110 can repeatedly update the model parameters 112 of the delivery time machine learning model, e.g., as new training examples become available. The training engine 110 can obtain new training examples, e.g., by monitoring the electronic medical record databases 106 to determine when data has been added to the electronic medical record databases which would enable generation of one or more new training examples. The training engine 110 can generate a training example by processing data extracted from the electronic medical record databases 106 to generate: (i) a training input to the delivery time machine learning model, including patient features characterizing a pregnant patient, and (ii) an actual delivery time of patient. The training engine 110 can update the model parameters of the delivery time machine learning model in response to determining that any appropriate criterion has been satisfied, e.g., in response to determining that at least as threshold number of new training examples have become available since the delivery time machine learning model was last trained.

In some implementations, the system 100 includes multiple delivery time machine learning models 114, i.e., rather than a single delivery time machine learning model 114. Each delivery time machine learning model 114 can have a respective set of model parameters 112 having different values than the model parameters 112 of each other delivery time machine learning model 114.

Each delivery time machine learning model can be specialized through training to generate predicted delivery times 116 for certain patient categories. In one example, the set of patient categories can include: (i) patients whose membranes have ruptured, and (ii) patients whose membranes have not ruptured. As another example, the set of patient categories can include: (i) a category for patients who have not received an intervention, and (ii) a respective patient category for each intervention in a set of interventions, where a patient is included in the category for an intervention if the patient has received the intervention. An "intervention" can refer to, e.g., the administration of a drug or medical procedure, e.g., an epidural, an induction, an augmentation, etc.

To generate a predicted delivery time 116 for a patient, the system 100 can determine a patient category for the patient based on the set of patient features 108, and then generate the predicted delivery time using the delivery time machine learning model associated with the patient category.

Each delivery time machine learning model 114 can be trained primarily (or totally) on training examples corresponding to patients included in the patient category associated with the delivery time machine learning model 114. Thus each delivery time machine learning model 114 can be specialized through training to generate accurate predictions for certain categories of patients.

Figure 2:
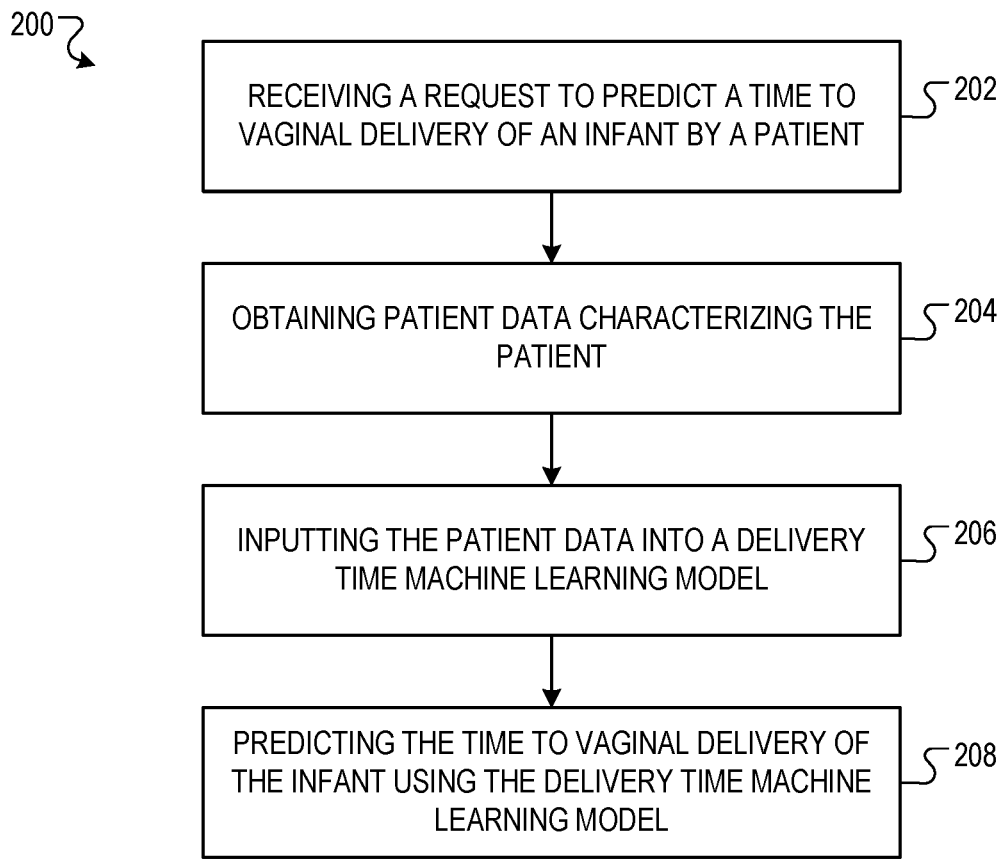
FIG. 2 is a flow diagram of an example process for predicting an amount of time until a patient gives birth.

FIG. 2 is a flow diagram of an example process 200 for predicting a time to vaginal delivery of an infant by a patient. For convenience, the process 200 will be described as being performed by a system of one or more computers located in one or more locations. For example, a delivery time prediction system, e.g., the delivery time prediction system 100 of FIG. 1, appropriately programmed in accordance with this specification, can perform the process 200.

The system receives a request to predict a time to vaginal delivery of an infant by a patient (202). The request can be generated, e.g., by a user of the system, or automatically generated, e.g., on a predefined schedule.

The system obtains patient data characterizing the patient (204). For instance, the system can obtain the patient data by querying one or more databases of electronic medical records. The patient data characterizing the patient can include a set of patient features.

The system inputs the patient data characterizing the patient into a delivery time machine learning model (206).

The system predicts the time to vaginal delivery of the infant using the delivery time machine learning model and the patient data inputted into the delivery time machine learning model (208). For instance, the system can process the patient data in accordance with values of a set of model parameters of the machine learning model to generate a prediction for the time to vaginal delivery of the infant.

The remainder of this specification further describes various possible implementations and aspects of the delivery time prediction system 100.

A better understanding of the expected time from admission to a vaginal delivery is required in order to facilitate a reduction in both unnecessary interventions during birth and the rate of primary cesarean deliveries. Consequently, the exemplary embodiments provide a process for health care providers and pregnant women that would provide the expected time from admission to the hospital to vaginal delivery of the infant.

A retrospective study was performed which reviewed over 70,000 patient charts and extracted each patient's examination and demographics (e.g., to generate a training example). The data was then used to develop (e.g., train) a multilinear regression model (e.g., as one example implementation of a delivery time machine learning model) to predict the expected time from admission to the hospital to vaginal delivery of the infant. A further objective is to optimize the admission time of patients for induction of labor, augmentation of labor or in spontaneous labor in regards to staffing and room availability.

Data was to be collected from patient's charts as provided by the Medical Records Department and the Cerner Powerchart EMR and Epic Systems (e.g., as examples of electronic medical record databases). As further examples, data can be collected from systems such as, e.g., inpatient EMR databases, outpatient EMR databases, etc. Data included but was not limited to the patients' hospital, cervical examination, gestational age, maternal age, presence of rupture of membranes, time of rupture of membranes, preeclampsia, chorioamnionitis, race, BMI, presence of epidural analgesia, the use of augmentation of labor, the time of starting augmentations, the use of cervical ripening agents, the time of starting cervical ripening agents, and birthweight of infant. (In some implementations, some or all of the described data is included in the patient features 108).

The patients studied were pregnant women who were between the ages of 12 to 55 years old. Inclusion criteria comprised early term to full term (37 weeks, 0 days to 41 weeks 6 days), vaginal delivery (CPT 59400 and 59409), Vaginal Birth after Cesarean Delivery (VBAC) (CPT 59618, 59620, 59622), Operative Delivery using Forceps/Vacuum (CPT 59409), singleton gestation and vertex (cephalic presentation) of fetus on admission.

Patients excluded exhibited criteria including preterm pregnancy, post-term pregnancy, operative vaginal deliveries, cesarean deliveries, intrauterine fetal demise, deliveries performed outside of a labor and delivery unit, multiple fetal gestation, patients without an examination on admission, patients without accurate gestational age dating, women less than 12 years old or greater than 55 years old, non-vertex presentation of fetus on admission, patients who had external cephalic version, shoulder dystocia on delivery on infant and patients with birth traumas.

The data collected was analyzed using t-test and multilinear regression model (e.g., as an example of a delivery time machine learning model). The data was also tested using logistic regression, decision tree, SVM algorithm, Naïve Bayes algorithm, KNN algorithm, K-means, Random forest algorithm, Dimensionality reduction algorithms, AdaBoosting algorithm and/or Gradient boosting algorithm (e.g., as examples of possible delivery time machine learning models). This compared the results from the patients' cervical examinations, characteristics of the study population, birthweights of the infants, and time from admission or start of induction of labor until vaginal delivery.

More particularly, factors analyzed included the following:

Dilation: dilation of the cervix
Effacement: thickness of the cervix
Fetal Station: the position of the infant's head in relation to the pelvis
Position: position of cervix (posterior, middle or anterior)
Consistency of cervix: feeling of cervix—firm, soft or in between
Prior deliveries: number of prior deliveries of patient
Cervical consistency: any medication to soften cervix and the times of each medication
Augmentation of labor: medicine to move labor along such as Pitocin
BMI: body mass index of patient
Maternal age: age of patient
Epidural analgesia: whether patient has been given an epidural or not for pain and the time of administration of the epidural
Race: race of patient
Existence of preeclampsia: existence of high blood pressure
Gestational age: number of weeks that patient is pregnant—37 weeks to 41 weeks and 6 days
Chorioamnionitis: presence of infection of uterus and if antibiotics administered
Fetal weight: the weight of the infant is an estimate which may be obtained from an ultrasound or Leopold's maneuver before the baby is delivered.

The patient features 108 described with reference to FIG. 1 can include some or all of the factors listed above.

The disclosed subject matter is directed to systems, computer-implemented methods, apparatus and/or computer program products that provide for managing an induction of labor, augmentation of labor and spontaneous labor and the intrapartum labor course using artificial intelligence (AI) analytics to facilitate more accurate predictions of the time to delivery of an infant, decreasing primary cesarean delivery rates and planning staffing of the labor and delivery unit. The disclosed techniques for predicting the time to delivery of an infant are designed to facilitate determining which patients require inductions of labor with cervical ripening, augmentation of labor, epidural placement, the timing when patients should be scheduled to arrive to the hospital, the timing when the delivering physician should arrive to the hospital, the number of nurses needed to staff the Labor and Delivery units, the number of hours a patient will occupy a Labor and Delivery room and provide an end goal for the expected time to delivery of the infant for patients to stay motivated during their intrapartum course. This will empower providers and nurses to take a holistic approach, using technology and people to address labor management.

In one or more embodiments, the disclosed techniques employ machine learning (ML) analysis of historical patients' admission data, patients' demographics and patients' intrapartum course for different patient groups and institutions as well as clinical domain knowledge (e.g. clinical standards, textbook clinical protocols and teaching materials, expert practitioner feedback, etc.) to provide an accurate analysis that measures and benchmarks the time to delivery of an infant and historically used Bishop Score system for a particular patient population. In addition, the disclosed application provides a full-service, real-time solution to aid healthcare organizations in extracting, organizing, reporting and translating pregnancy delivery and electronic medical record (EMR) data into actionable clinical practices to improve quality of care (through standardization and per patient tailoring) and drive economic and medical efficiency.

Thus, while one exemplary embodiment may be on an HTM, JAVA, Android or iOS platform for access by medical professionals another exemplary embodiment may link with EMR data to both retrieve patient data and input patient data to the EMR source.

The DTA can integrate and interface with the patient's EMR to provide the estimated time to delivery, Bishop score and decision trees to providers, thereby promoting evidence-based clinical practice. (The DTA can refer to some or all of the operations implemented by the delivery time prediction system 100 described with reference to FIG. 1). The DTA may pull populated clinical data directly from patients' electronic medical records using electronic medical records systems such as SMART Health IT, Clinical Decision Support Systems (CDSS), LOINC (Logical Observation Identifiers Names and Codes), the HL7 (Health Line Seven) interface engine, HL7 FHIR (Fast Healthcare Interoperability Resources), Integrating the Healthcare Enterprise's (IHE's) Cross-Enterprise Document Sharing (XDS), C-CDA (HL7 Consolidated Clinical Document Architecture), Patient Identifier Cross-Referencing/Patient Demographics Query (PIX/PDQ), Laboratory (LAB), Audit Trail and Node Authentication (ATNA) and Digital Imaging and Communications in Medicine (DICOM) (e.g., by way of the feature generation engine described with reference to FIG. 1). The data may then be integrated into the DTA's calculators and application and provide a predicted time to delivery to the patient's EMR.

As an example, SMART Health IT is an open, standards-based technology platform that enables innovators to create apps that seamlessly and securely run across the healthcare system. Using an electronic health record (EHR) system or data warehouse that supports the SMART standard, patients, doctors, and healthcare practitioners can draw on this library of apps to improve clinical care, research, and public health.

The SMART platform is composed of open standards, open source tools for developers building apps and a publicly accessible app gallery. To date, dozens of clinical applications have been built on this platform, and SMART applications are being used to provide clinical care at healthcare institutions.

The predicted time to delivery resulting from the DTA may be provided back to the EMR using these electronic medical record systems.

With the information provided from the DTA, the patient's EMR will provide user functionality to trigger clinical decision tools including preparing the operating room for a possible cesarean section, suggesting cervical ripening agents for induction of labor, suggesting the initiation of labor augmentation using oxytocin and other decision making trees. The user functionality will also allow for a plug-and-play cloud-based integration platform that facilitates rapid provision of data that will interface with the DTA to provide the endpoints for the estimated time to delivery and bishop score. The SMART on FHIR API (application programming interface) will allow for an open and standards-based API which will allow the DTA to run anywhere in the healthcare system.

The disclosed labor management techniques were developed with some key drivers in mind. The key drivers include, but are not limited to, the need to (1) clearly define induction of labor, natural labor and augmentation of labor standards and appropriateness exceptions, (2) ensure that there is staff knowledge in the labor and admission standard expectations, (3) ensure that there is staff knowledge in the cervical and pelvic examination of patients, (4) develop a measurement system that can be filtered by examinations, admission criteria, demographics, intrapartum interventions, providers, facility, actual time to delivery of infant, etc., (5) ensure that staff and patients are aware of the process and outcome measurements, and (6) continual learning through case reviews and updated pregnancy-related guidelines as released by ACOG (American College of Obstetricians and Gynecologists), American Journal of Obstetrics and Gynecology, Society for Maternal and Fetal Medicine, National Center for Health Statistics, Hospital-related guidelines and other related publications.

The present teaching is built on the premise that cesarean delivery decisions for labor dystocia (the abnormal progression of the stages of labor) and that the estimated time to delivery are influenced by evidence-based knowledge that accounts for individual patient variables, and not solely on provider preference or behavior. This is accomplished in part through the development and application of a delivery time prediction system 100 that computes the time to delivery of infants by factoring evidenced-based knowledge (patient demographics, pelvic and physical examination, estimated fetal weighs, records of similar patients' outcomes, risk factors, other comorbidities, etc.) and input from practitioners in obstetrics. The ML model/algorithm is referred to herein as the Delivery Time Algorithm (DTA) (delivery time prediction system 100).

In addition to determining the time to delivery of an infant and Bishop Score based on the cervical examination, the evidence based knowledge and input used by the DTA may also be critical in determining who should have a cesarean delivery, viable candidates for a normal spontaneous vaginal delivery, and/or the maximum number of hours a provider can expect for a patient to have a safe normal spontaneous vaginal delivery. In this regard, through the use of the DTA, the disclosed techniques can reduce primary cesarean delivery rates, allow physicians to schedule their patients based on the expected time to delivery, plan an on-call day, decrease the cesarean section rates for labor dystocia and maternal requests. The nurse managers and nurses are able to determine the number of nurses needed to staff a Labor and Delivery unit and allocate patients to rooms based on the time to delivery. Patients are able to utilize the DTA to have an end goal and decrease the uncertainty of the labor process.

In one or more embodiments, the disclosed systems can mine and correlate data from multiple data sources (e.g., EMRs, labor and delivery charts, prenatal records, surgical systems, financial systems) to determine the expected time to delivery for individual patients and different patient groups. The expected time to delivery and Bishop Score can be outputs (results) presented to care providers as scientific-based evidence in determining how to proceed with labor-related cases (e.g., cervical ripening, induction of labor, augmentation of labor and natural labor). In some examples, the results of the DTA can be integrated with and visualized within the dashboard of the provider's EMR, allowing the provider to make intelligent decisions at the point of care. Information regarding the inferred risks and expected outcomes can also be incorporated into the ML process so that the DTA can be adjusted to more closely reflect the expected outcomes and risks. In some implementations, the disclosed techniques can further apply the results of the DTA to predict a provider's schedule, staffing requirements and costs of the infant's delivery depending on route (vaginal delivery or cesarean delivery). These cost related metrics can also be viewed in the dashboard and utilized to further evaluate the cost of delivery of the infant.

In yet another embodiment, labor-related data that is determined via the application of the DTA can be used to determine staffing requirements in real-time (e.g., physicians, physician assistants (PAs), nurses (RNs), etc.). In this regard, information regarding expected time to delivery pertaining to a particular patient can be used to determine how to allocate staff in real-time. The guidelines and staffing can be adjusted to account for the new insights provided by the DTA based on data from many different locations, regions and patient populations. The system can also determine the expected staff demands and automatically adjust staffing and patient scheduling to improve patient care while minimizing a waste of staffing resources.

In various embodiments, the patient data includes information for a patient that is a potential candidate for a normal spontaneous vaginal delivery, operative vaginal delivery using vacuum or forceps, or vaginal birth after cesarean delivery and includes a variety of rich information about the patient that can influence on a per patient basis with respect to their tailored criteria, the estimated time to vaginal delivery of an infant. The delivery time analysis can further process the patient data using one or more ML and AI tactics to evaluate the appropriateness of cervical ripening, induction of labor and augmentation of labor, and provide a recommendation regarding whether to proceed with a trial of labor and/or the estimated time to delivery.

The patient data (patient features 108) can include information regarding the current clinical state, status and/or condition of the patient and the current course of treatment of the patient. Such information can include, but is not limited to: diagnosis information (e.g., any current clinical diagnosis of the patient condition by diagnosis code, diagnosis related group (DRG) etc.), patient's gestational age, patient's age, patient's race, patient's prior pregnancy history including parity, clinical examination (vitals, relevant laboratory measures, physical examinations), reason for admittance, location of admittance, current course of treatment/care (e.g., including whether the patient is receiving interventions for cervical consistency such as a cervical foley catheter, Misoprostol, Dinoprostone, oxytocin, etc.), the type of medications administered for augmentation of labor, whether epidural analgesia was administered, antibiotics given for prophylaxis of Group Beta Strep colonization, etc. Information regarding clinical examination can include but is not limited to cervical dilation, cervical effacement, fetal station, cervical consistency and cervical position. The patient data can also include real-time physiological information capture for a patient regarding monitored/reported vital signs, including but not limited to: heart rate, respiratory rate, temperature, systolic blood pressure, diastolic blood pressure, and other biomedical/physiologic status data that can be captured and/or monitored for a patient in real-time (e.g., via one of more medical monitoring devices, fetal heart rate monitoring, tocometers, fetal scalp electrode and implantable medical devices (IMDs, and the like). In various implementations, these physiologic parameters can include real-time measures tracked and received for the patient over a period of time and thus provide a measure of changes in the physiological parameters over the course of the patient's care.

The patient data (patient features 108) can also include relevant medical history information for a patient. For example, the relevant medical history information can include information regarding underlying conditions/comorbidities (e.g., preeclampsia, chorioamnionitis, diabetes, anemia, and other relevant comorbidities), past treatments, past procedures/surgeries (e.g., prior cesarean deliveries, prior termination of pregnancies, prior miscarriages, cerclage placement and removal, and information regarding location, timing and type of procedures), past diagnosis, family history, known allergies, past laboratory tests and associated results/reports and past imaging studies and associated results/reports. In various embodiments, the medical history information can be extracted from one or more EMRs and/or electronic health records (EHRs) for the patient.

In various embodiments, the reception component can regularly and/or continuously receive the various types of patient data discussed above from a variety of patient data systems/sources in real-time. For example, the reception component can receive the patient information from one or more from EMR systems, scheduling systems, blood banks, admission systems, financial systems, insurance systems, coding systems, physician notes/reports, laboratory report systems, imaging systems, case worker reports, case status tracking systems, patient location tracking systems/devices, patient vital signs monitoring systems, medical monitoring devices associated with the patients, and the like. In some implementations, these tracking and/or monitoring systems/devices can include systems/devices configured to receive and report user input in real-time explicitly identifying and/or indicating such status information (e.g., regarding the patient's active case status, location, workflow event progress, staff involved, etc.). These tracking and/or monitoring systems/devices can also include intelligent systems/devices configured to determine and report various real-time status information without or with minimal manual input based on analysis of sensor/device captured data signals. For example, these tracking and/or monitoring systems/devices can also include systems/devices configured determine information regarding what's currently happening to the patient (e.g., workflow events), where the patient is currently located, who is currently treating/attending to the patient, and the like based on analysis of a variety of captured data, including but not limited to: image data (e.g., using object recognition and/or other image pattern recognition technologies), audio data (e.g., using speech to text and natural language processing NPL), motion sensor data (e.g., using motion pattern recognition technology), radio frequency (RF) data, temperature sensor data, light sensor data, infrared (IR) senor data, biometric sensor data, and the like.

In this regard, the reception component can collect, extract or otherwise receive patient data continuously and/or regularly over the course of operation of a medical system/facility as the patient data is generated by and/or entered into the one or more current state data systems/sources. For example, in some implementations, the reception component can repeatedly extract, collect or otherwise receive patient data for all or specific patients and/or patient groups according to a defined schedule (e.g., every second, every few seconds, every minute, every five minutes, every ten minutes, etc.). In other implementations, the reception component can receive (e.g., in a push fashion) patient data reflecting any changes to the current state of a patient as they occur (e.g., in response to entry into and/or generation by the one or more current state data sources/systems).

In some implementations, as noted previously, the DTA is derived from multiple linear regression. Regression models are used to describe relationships between variables by fitting a line to the observed data. Regression allows you to estimate how a dependent variable changes as the independent variable(s) change.

Multiple linear regression is used to estimate the relationship between two or more independent variables and one dependent variable. You can use multiple linear regression when you want to know:

How strong the relationship is between two or more independent variables and one dependent variable and/or The value of the dependent variable at a certain value of the independent variables.

The formula for a multiple linear regression is:

$$Y=\beta 0+\beta 1 X1+ \ldots +\beta n Xn+\varepsilon$$

where

Y=the predicted value of the dependent variable

β0=the y-intercept of the regression equation (value of y when all other parameters are set to 0)

β1X1=the regression coefficient (β1) of the first independent variable (X1) (a.k.a. the effect that increasing the value of the independent variable has on the predicted y value)

. . .

βnXn=the regression coefficient of the last independent variable

ε=model error (e.g., how much variation there is in our estimate of y).

To find the best-fit line for each independent variable, multiple linear regression calculates three things:

The regression coefficients that lead to the smallest overall model error.

The t-statistic of the overall model.

The associated p-value (how likely it is that the t-statistic would have occurred by chance if the null hypothesis of no relationship between the independent and dependent variables was true).

It then calculates the t-statistic and p-value for each regression coefficient in the model.

A sample table for results from a multiple linear regression of historical patient data is illustrated in FIG. 3 where the coefficient is the regression coefficient, the standard error column displays the standard error of the estimate of the regression coefficient, the t value column displays the test statistic and the p-value. The results are not actually shown in this table.

In the exemplary embodiments, the dependent variable is the time to delivery of the infant during vaginal delivery, which is now the DTA. For purposes of the DTA in the exemplary embodiments, the y intercept and the model error have been combined and just appear as the y intercept.

In some implementations, the full DTA may appear as follows:

$$DTA=\beta 0+(dilation \times \beta 1 X1)+(effacement \times \beta 2 X2)+(fetal\ station \times \beta 3 X3)+(position \times \beta 4 X4)+(consistency \times \beta 5 X5)+(prior\ deliveries \times \beta 6 X6)+(cervical\ consistency \times \beta 7 X7)+(augmentation \times \beta 8 X8)+(BMI \times \beta 9 X9)+(maternal\ age \times \beta 10 X10)+(epidural\ analgesia \times \beta 11 X11)+(race \times \beta 12 X12)+(preeclampsia \times \beta 13 X13).$$

Measurements obtained from EMR, hospital records, admission information and other sources for each of dilation, effacement, fetal station, position, consistency, prior deliveries, cervical ripening, augmentation, BMI, maternal age, epidural analgesia, race and preeclampsia would be inserted in the DTA. If the factors of gestational age, chorioamnionitis and fetal weight become statistically significant then measurements for each of gestational age, chorioamnionitis and fetal weight along with their regression coefficients would be included in the DTA.

Figure 4:
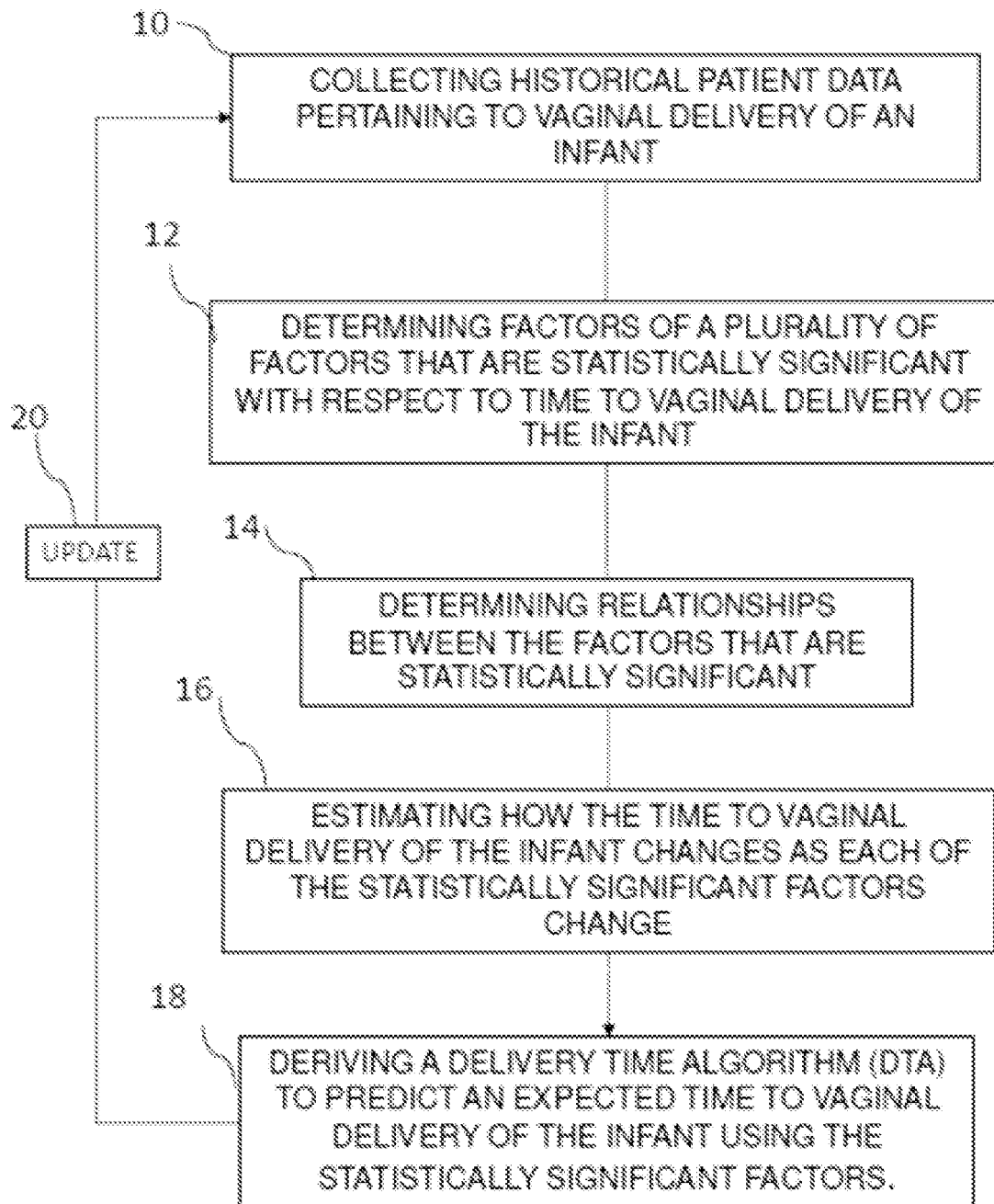
FIG. 4 is a flow chart illustrating one exemplary embodiment of the disclosed techniques.

Referring to FIG. 4, there is illustrated an exemplary embodiment of a method of predicting the time for vaginal delivery which includes collecting historical patient data from past patients pertaining to vaginal delivery of an infant, box 10. The historical patient data refers to the collected patient data from the retrospective study discussed above. The patient data from the present patient may also be added to the historical patient data since the historical patient data may be updated to include present and future patent data as well as past patient data.

Then, determining factors of a plurality of factors that are statistically significant with respect to time to vaginal delivery of the infant, box 12. The factors may be those shown in FIG. 1 which may be statistically significant. As noted previously, the gestational age, chorioamnionitis and fetal weight factors may not be statistically significant. In future iterations, one or more of the factors shown in FIG. 1 may become statistically insignificant. A factor can be said to be statistically significant with respect to time to vaginal delivery of the infant, e.g., if a significance factor derived from a statistical significance test satisfies a threshold. For instance, the significance factor can be a p-value, and the threshold can be 0.05.

In a next step, determining relationships between the factors that are statistically significant, box 14.

In a further step of the process, estimating how the time to vaginal delivery of the infant changes as each of the statistically significant factors change, box 16.

In the next step, deriving a delivery time algorithm (DTA) to predict an expected time to vaginal delivery of the infant using the statistically significant factors, box 18.

In one preferred exemplary embodiment, the method may loop back to collecting historical patient data to either continually or intermittently update the historical patient data collected, box 20.

In some implementations, the DTA may be derived using the multiple linear regression discussed above.

Figure 5:
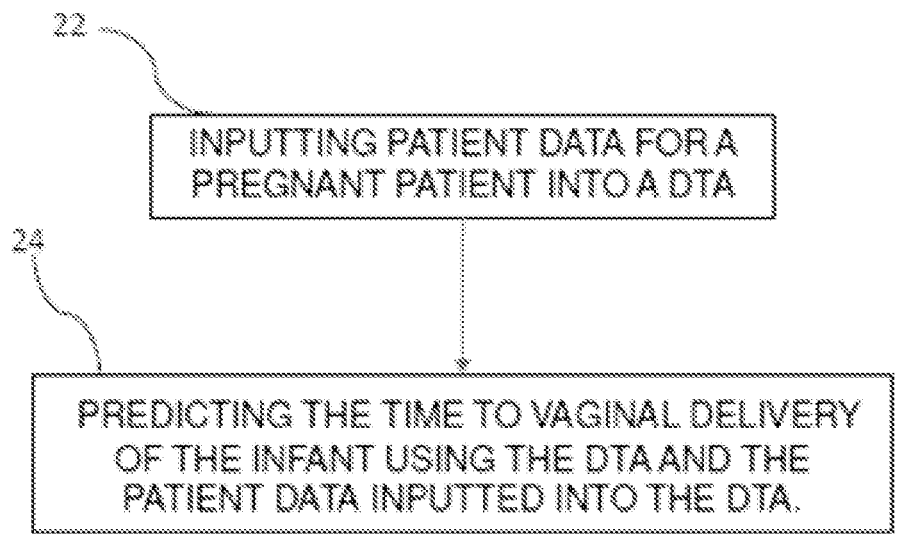
FIG. 5 is another flow chart illustrating another exemplary embodiment of the disclosed techniques.

Referring to FIG. 5, there is illustrated another exemplary embodiment of a method of predicting the time to vaginal delivery of an infant which includes inputting patient data for a pregnant patient into a DTA, box 22.

In a further step, there is included the step of predicting the time to vaginal delivery of the infant using the DTA and the patient data inputted into the DTA, box 24.

Based on using the DTA in practice with over 500 patients, the DTA has been found to accurately predict time to vaginal delivery of an infant to within 1.75 hours of actual vaginal delivery. It is expected that with further use and analysis in conjunction with pregnant patients, the discrepancy between actual vaginal delivery and the DTA predicted time to vaginal delivery may be reduced.

Figure 6:
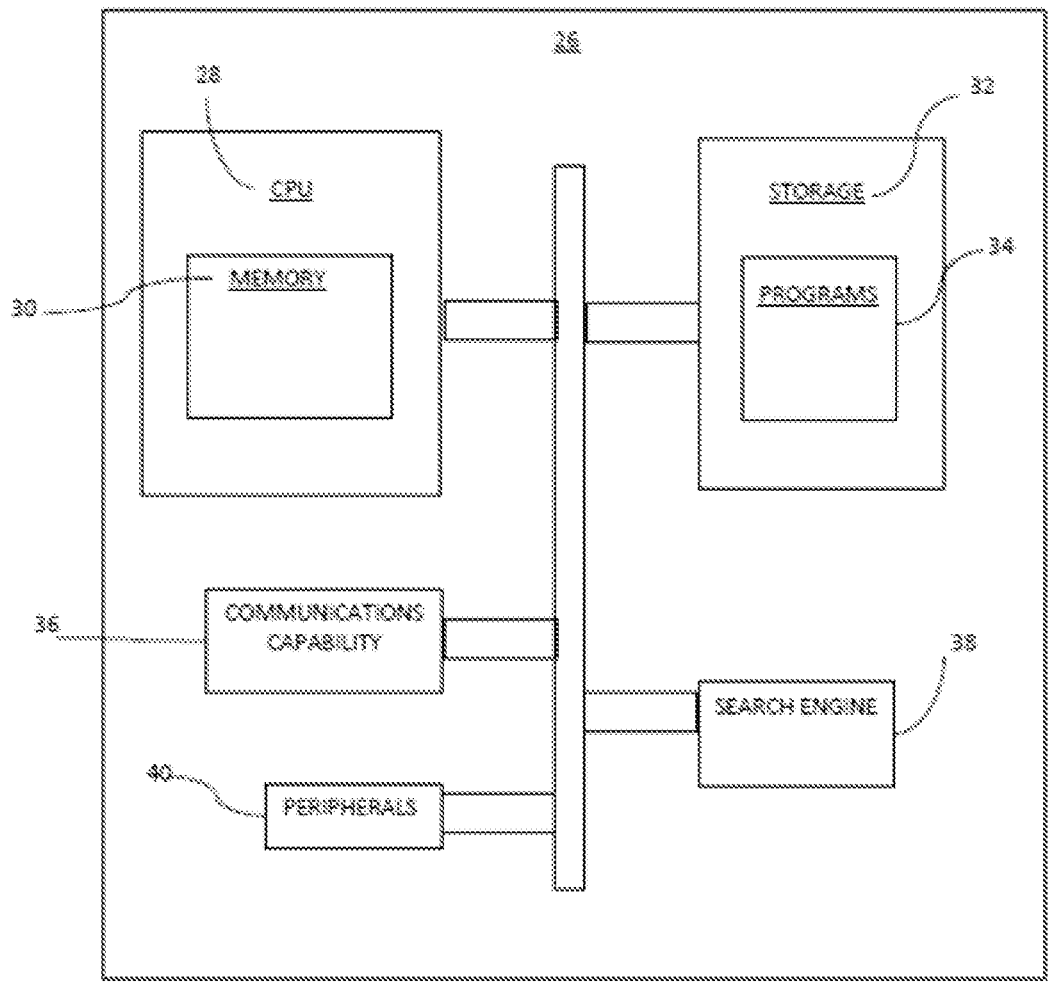
FIG. 6 is an illustration of an electronic device for implementing the exemplary embodiments.

Referring now to FIG. 6, there is shown an electronic device 26 for implementing the exemplary embodiments. The electronic device 26 may include a central processing unit (CPU) 28 having memory 30.

Further contained within electronic device 26 may be storage 32. Alternatively, storage 32 may be remotely connected to electronic device 26. Contained within storage 32 may be programs 34 having program instructions to perform various tasks.

The electronic device 26 may further include communications capability instructions 36 to allow electronic device 26 to communicate with the outside world such as by WiFi, cellular, satellite, wired or short range radio capabilities. There may also be search engine instructions 38 to search the Internet and to provide browsing capability to the electronic device 26.

Additionally, electronic device 26 may have peripherals instructions 40 to operate peripheral components such as a display, keyboard, mouse and printer.

One or more embodiments described herein can be a system, a method, an apparatus and/or a computer program product at any possible technical detail level of integration. The computer program product can include a computer readable storage medium (or media) having computer readable program instructions thereon for causing a processor to carry out aspects of one or more embodiment. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. In this regard, in various embodiments, a computer readable storage medium as used herein can include non-transitory and tangible computer readable storage mediums.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of one or more embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Python, HTML, Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of one or more embodiments.

Aspects of one or more embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and other devices to function in a particular manner, such that the computer readable storage medium having instructions stored therein comprises an article of manufacture including instructions which implement aspects of the function/act specified in the flowchart and block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and block diagram block or blocks.

While the subject matter has been described above in the general context of computer-executable instructions of a computer program product that runs on one or more computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and a computer. By way of illustration, both an application running on a server and the server can be a component. One or more components can reside within a process or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal).

As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that can provide specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches, and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM).

Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

It will be apparent to those skilled in the art having regard to this disclosure that other modifications of the exemplary embodiments beyond those embodiments specifically described here may be made without departing from the spirit of the disclosure.

What is claimed is:

1. A method performed by one or more computers, the method comprising:
   receiving a request to predict a time to vaginal delivery of an infant by a patient; and
   in response to receiving the request, generating a sequence of multiple delivery time predictions for the time to vaginal delivery of the infant by the patient, comprising, for each of a plurality of time points in a sequence of multiple time points:
      determining, based at least in part on automated and continuous monitoring of real-time sensor data that is generated by one or more sensors and that characterizes a current physiological state of the patient, that a criterion for generating a new delivery time prediction for the time to vaginal delivery of the infant using a delivery time machine learning model has been satisfied; and
      in response to determining, based at least in part on automated and continuous monitoring of real-time sensor data that is generated by one or more sensors and that characterizes the current physiological state of the patient, that the criterion for generating the new delivery time prediction for the time to vaginal delivery of the infant using the delivery time machine learning model has been satisfied:
         generating a current model input that characterizes a current state of the patient by automatically querying a database storing one or more electronic medical records of the patient;
         processing the current model input using the delivery time machine learning model, in accordance with trained values of a set of model parameters of the delivery time machine learning model, to generate a prediction for the time to vaginal delivery of the infant, and
         generating a notification that indicates the prediction for the time to vaginal delivery of the infant;
   wherein training the delivery time machine learning model comprises:
      obtaining a set of training samples, wherein each training sample comprises: (i) a model input to the delivery time machine learning model that characterizes features of an individual, and (ii) a target delivery time that defines a time to vaginal delivery of the individual; and
      training the delivery time machine learning model on the set of training samples by a machine learning technique, the training comprising, for each training sample:
         training the delivery time machine learning model to minimize an error between: (a) a predicted delivery time that is generated by processing the model input of the training sample using the delivery time machine learning model, and (b) the target delivery time for the training sample;
   wherein training the delivery time machine learning model further comprises:
      dynamically monitoring one or more electronic medical record databases to determine when new electronic medical record data has been added to the one or more electronic medical records databases that enables the generation of new training samples for training the delivery time machine learning model;
      automatically generating new training samples for training the delivery time machine learning model as new electronic medical record data is added to the one or more electronic medical record databases; and
      re-training the delivery time machine learning model in response to determining that at least a threshold number of new training examples have been generated since the delivery time machine learning model was last trained.

2. The method of claim 1, further comprising, at one or more of the plurality of time points:
   determining a current patient category of the patient based on current values of a set of features of the patient; and
   selecting the delivery time machine learning model, from a set of delivery time machine learning models, based on the current patient category of the patient.

3. The method of claim 2, wherein the current patient category of the patient characterizes a current physiological state of the patient.

4. The method of claim 1, wherein for each of one or more time points, determining that a criterion for generating a new delivery time prediction for the time to vaginal delivery of the infant has been satisfied comprises:
   determining that a value of a feature characterizing the patient has changed by at least a threshold amount since the time to vaginal delivery of the infant was previously predicted.

5. The method of claim 1, wherein for each of one or more of the time points, generating the current model input to the delivery time machine learning model further comprises:
   obtaining current sensor data generated by one or more sensors located on or in proximity to the patient; and
   including the current sensor data in the current model input to the delivery time machine learning model.

6. The method of claim 1, wherein for one or more time points in the sequence of time points, the generating the prediction for the time to vaginal delivery of the infant comprises:
   generating a prediction for an amount of time until vaginal delivery of the infant after a cervix of the patient dilates to a predefined amount; or
   generating a prediction for an amount of time until vaginal delivery of the infant after the patient is admitted to a hospital; or
   generating a prediction for an amount of time until vaginal delivery of the infant after the patient enters into labor.

7. The method of claim 1, further comprising, for each of one or more time points in the sequence of time points:
   automatically storing the prediction for the time to vaginal delivery of the infant generated at the time point in an electronic medical record of the patient.

8. The method of claim 1, further comprising, at one or more time points in the sequence of time points:
   generating a respective importance score for each of a plurality of features included in a model input to the delivery time machine learning model;
   wherein the importance score for a feature measures an impact of the feature on a prediction for time to vaginal delivery of the infant generated by the delivery time machine learning model by processing the model input.

9. The method of claim 1, further comprising, for one or more time points in the sequence of time points, determining that a second criterion for generating a new delivery time for the time to vaginal delivery of the infant has been satisfied, comprising:

determining that a threshold duration of time has elapsed since the time to vaginal delivery of the infant was previously predicted.

10. The method of claim 1, wherein the delivery time machine learning model includes one or more of: a neural network model, a random forest model, a support vector machine model, or a linear regression model.

11. The method of claim 1, wherein generating the notification that indicates the prediction for the time to vaginal delivery of the infant comprises:
transmitting the notification over a data communications network; and
causing the notification to be presented to a user by way of an application.

12. The method of claim 1, further comprising, for one or more time points in the sequence of time points, after generating the prediction for the time to vaginal delivery of the infant:
automatically interfacing with a resource reservation system to reserve one or more resources related to delivery of the infant in a time window based on the prediction for the time to vaginal delivery of the infant.

13. The method of claim 12, wherein automatically interfacing with the resource reservation system to reserve one or more resources related to delivery of the infant in the time window based on the prediction for the time to vaginal delivery of the infant comprises:
automatically reserving a delivery room in the time window based on the new prediction for the time to vaginal delivery of the infant.

14. The method of claim 1, further comprising, for one or more time points in the sequence of time points, after generating the prediction for the time to vaginal delivery of the infant:
determining that vaginal delivery of the infant has not occurred within a threshold duration of time following the prediction for the time to vaginal delivery of the infant; and
automatically generating a notification indicating that vaginal delivery of the infant has not occurred within the threshold duration of time following the prediction for the time to vaginal delivery of the infant.

15. The method of claim 1, further comprising, at one or more time points in the sequence of time points:
generating a confidence estimate that measures a confidence of the delivery time machine learning model in the prediction, generated at the time point, for the time to vaginal delivery of the infant.

16. A system comprising:
one or more computers; and
one or more storage devices communicatively coupled to the one or more computers, wherein the one or more storage devices store instructions that, when executed by the one or more computers, cause the one or more computers to perform operations comprising:
receiving a request to predict a time to vaginal delivery of an infant by a patient; and
in response to receiving the request, generating a sequence of multiple delivery time predictions for the time to vaginal delivery of the infant by the patient, comprising, for each of a plurality of time points in a sequence of multiple time points:
determining, based at least in part on automated and continuous monitoring of real-time sensor data that is generated by one or more sensors and that characterizes a current physiological state of the patient, that a criterion for generating a new delivery time prediction for the time to vaginal delivery of the infant using a delivery time machine learning model has been satisfied; and
in response to determining, based at least in part on automated and continuous monitoring of real-time sensor data that is generated by one or more sensors and that characterizes the current physiological state of the patient, that the criterion for generating the new delivery time prediction for the time to vaginal delivery of the infant using the delivery time machine learning model has been satisfied:
generating a current model input that characterizes a current state of the patient by automatically querying a database storing one or more electronic medical records of the patient;
processing the current model input using the delivery time machine learning model, in accordance with trained values of a set of model parameters of the delivery time machine learning model, to generate a prediction for the time to vaginal delivery of the infant, and
generating a notification that indicates the prediction for the time to vaginal delivery of the infant;
wherein training the delivery time machine learning model comprises:
obtaining a set of training samples, wherein each training sample comprises: (i) a model input to the delivery time machine learning model that characterizes features of an individual, and (ii) a target delivery time that defines a time to vaginal delivery of the individual; and
training the delivery time machine learning model on the set of training samples by a machine learning technique, the training comprising, for each training sample:
training the delivery time machine learning model to process the model input of the training sample to generate a predicted delivery time that is substantially similar to the target delivery time for the training sample;
wherein training the delivery time machine learning model further comprises:
dynamically monitoring one or more electronic medical records databases to determine when new electronic medical record data has been added to the one or more electronic medical records databases that enables the generation of new training samples for training the delivery time machine learning model;
automatically generating new training samples for training the delivery time machine learning model as new electronic medical record data is added to the one or more electronic medical record databases; and
re-training the delivery time machine learning model in response to determining that at least a threshold number of new training examples have been generated since the delivery time machine learning model was last trained.

17. The system of claim 16, wherein the operations further comprise, for one or more time points in the sequence of time points, after generating the prediction for the time to vaginal delivery of the infant:
automatically interfacing with a resource reservation system to reserve one or more resources related to delivery of the infant in a time window based on the prediction for the time to vaginal delivery of the infant.

18. The system of claim 17, wherein automatically interfacing with the resource reservation system to reserve one or more resources related to delivery of the infant in the time window based on the prediction for the time to vaginal delivery of the infant comprises:
automatically reserving a delivery room in the time window based on the new prediction for the time to vaginal delivery of the infant.

19. One or more non-transitory computer storage media storing instructions that when executed by one or more computers cause the one or more computers to perform operations comprising:
receiving a request to predict a time to vaginal delivery of an infant by a patient; and
in response to receiving the request, generating a sequence of multiple delivery time predictions for the time to vaginal delivery of the infant by the patient, comprising, for each of a plurality of time points in a sequence of multiple time points:
determining, based at least in part on automated and continuous monitoring of real-time sensor data that is generated by one or more sensors and that characterizes a current physiological state of the patient, that a criterion for generating a new delivery time prediction for the time to vaginal delivery of the infant using a delivery time machine learning model has been satisfied; and
in response to determining, based at least in part on automated and continuous monitoring of real-time sensor data that is generated by one or more sensors and that characterizes the current physiological state of the patient, that the criterion for generating the new delivery time prediction for the time to vaginal delivery of the infant using the delivery time machine learning model has been satisfied:
generating a current model input that characterizes a current state of the patient by automatically querying a database storing one or more electronic medical records of the patient;
processing the current model input using the delivery time machine learning model, in accordance with trained values of a set of model parameters of the delivery time machine learning model, to generate a prediction for the time to vaginal delivery of the infant, and
generating a notification that indicates the prediction for the time to vaginal delivery of the infant;
wherein training the delivery time machine learning model comprises:
obtaining a set of training samples, wherein each training sample comprises: (i) a model input to the delivery time machine learning model that characterizes features of an individual, and (ii) a target delivery time that defines a time to vaginal delivery of the individual; and
training the delivery time machine learning model on the set of training samples by a machine learning technique, the training comprising, for each training sample:
training the delivery time machine learning model to process the model input of the training sample to generate a predicted delivery time that is substantially similar to the target delivery time for the training sample;
wherein training the delivery time machine learning model further comprises:
dynamically monitoring one or more electronic medical records databases to determine when new electronic medical record data has been added to the one or more electronic medical records databases that enables the generation of new training samples for training the delivery time machine learning model;
automatically generating new training samples for training the delivery time machine learning model as new electronic medical record data is added to the one or more electronic medical record databases; and
re-training the delivery time machine learning model in response to determining that at least a threshold number of new training examples have been generated since the delivery time machine learning model was last trained.

20. The non-transitory computer storage media of claim 19, wherein the operations further comprise, for one or more time points in the sequence of time points, after generating the prediction for the time to vaginal delivery of the infant:
automatically interfacing with a resource reservation system to reserve one or more resources related to delivery of the infant in a time window based on the prediction for the time to vaginal delivery of the infant.

* * * * *